(12) United States Patent
Wu et al.

(10) Patent No.: US 10,537,260 B2
(45) Date of Patent: Jan. 21, 2020

(54) VARYING DIAMETER CATHETER DISTAL END DESIGN FOR DECREASED DISTAL HUB SIZE

(71) Applicant: Biosense Webster (Israel) Ltd., Yokneam (IL)

(72) Inventors: Steven Wu, San Jose, CA (US); Sungwoo Min, Fullerton, CA (US); Vishav Aujla, Valencia, CA (US); Neil Merchant, Pasadena, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 454 days.

(21) Appl. No.: 15/148,146

(22) Filed: May 6, 2016

(65) Prior Publication Data

US 2017/0319139 A1    Nov. 9, 2017

(51) Int. Cl.
| | | |
|---|---|---|
| *A61B 5/042* | (2006.01) | |
| *A61B 5/00* | (2006.01) | |
| *A61B 18/14* | (2006.01) | |
| *A61B 18/00* | (2006.01) | |
| *A61M 25/00* | (2006.01) | |
| *A61B 17/00* | (2006.01) | |
| *A61B 5/06* | (2006.01) | |

(52) U.S. Cl.
CPC .......... *A61B 5/0422* (2013.01); *A61B 5/6858* (2013.01); *A61B 5/6859* (2013.01); *A61B 18/00* (2013.01); *A61B 18/1492* (2013.01); *A61M 25/0009* (2013.01); *A61B 5/0036* (2018.08); *A61B 5/062* (2013.01); *A61B 2017/00053* (2013.01); *A61B 2017/00867* (2013.01); *A61B 2018/0016* (2013.01); *A61B 2018/00267* (2013.01); *A61B 2018/00351* (2013.01); *A61B 2218/002* (2013.01)

(58) Field of Classification Search
CPC .... A61B 5/0422; A61B 5/6858; A61B 5/6859
See application file for complete search history.

(56) References Cited

U.S. PATENT DOCUMENTS

| | | | |
|---|---|---|---|
| 5,391,199 A | 2/1995 | Ben-Haim | |
| 5,772,590 A | 6/1998 | Webster | |
| 5,911,739 A | 6/1999 | Kordis et al. | |
| 6,064,905 A | 5/2000 | Webster et al. | |

(Continued)

FOREIGN PATENT DOCUMENTS

| | | |
|---|---|---|
| EP | 2848226 A1 | 3/2015 |
| WO | 96/05768 | 2/1996 |

(Continued)

OTHER PUBLICATIONS

European Search Report and Written Opinion for European Application No. 17169660.2, dated Oct. 4, 2017.

*Primary Examiner* — Lee S Cohen
(74) *Attorney, Agent, or Firm* — Dergosits & Noah LLP; Todd A. Noah

(57) ABSTRACT

This disclosure is directed to a catheter having a basket-shaped electrode assembly with a high electrode density. The basket-shaped electrode assembly may have a plurality of spines, such as up to twelve, each with a plurality of electrodes, such as up to sixteen. The distal ends of the plurality of spines are joined at a distal hub, all of which are fashioned from a single piece of superelastic material.

19 Claims, 6 Drawing Sheets

(56) References Cited

U.S. PATENT DOCUMENTS

| | | | |
|---|---|---|---|
| 6,239,724 B1 | 5/2001 | Doron | |
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 6,748,225 B1 | 6/2004 | Kepler | |
| 6,973,340 B2 | 12/2005 | Fuimaono et al. | |
| 8,825,130 B2 * | 9/2014 | Just | A61B 18/1492 600/374 |
| 9,408,663 B2 * | 8/2016 | Hall | A61B 5/0422 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2013/0172715 A1 | 7/2013 | Just et al. | |
| 2014/0305699 A1 | 10/2014 | Govari | |
| 2014/0309512 A1 | 10/2014 | Govari et al. | |
| 2015/0223757 A1 * | 8/2015 | Werneth | A61B 5/6852 600/301 |
| 2015/0342532 A1 * | 12/2015 | Basu | A61B 5/6858 600/374 |
| 2017/0273738 A1 * | 9/2017 | Wu | A61B 5/6859 |

FOREIGN PATENT DOCUMENTS

| | | |
|---|---|---|
| WO | 09/72039 A2 | 6/2009 |
| WO | 15/77816 A1 | 6/2015 |

\* cited by examiner

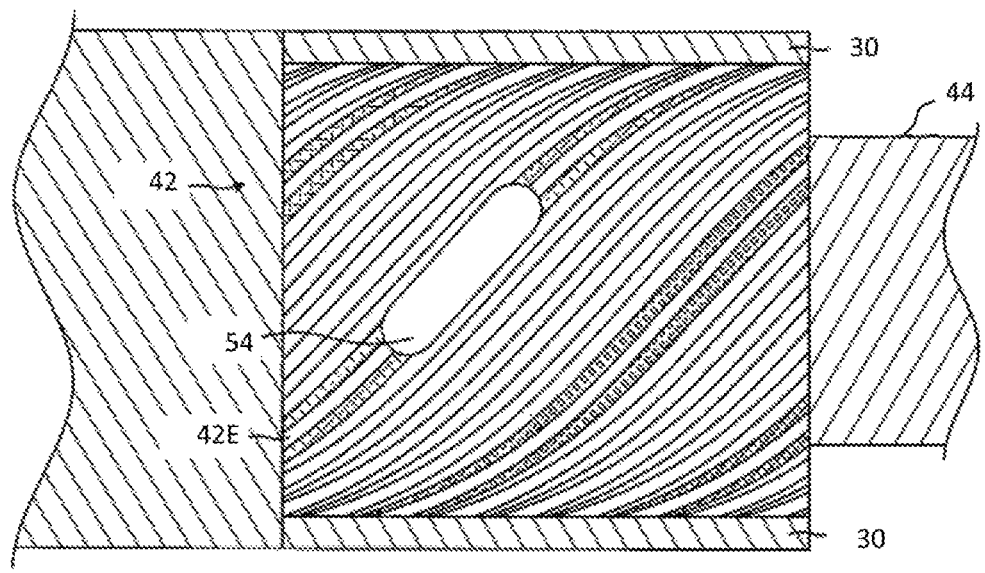
FIG. 6A
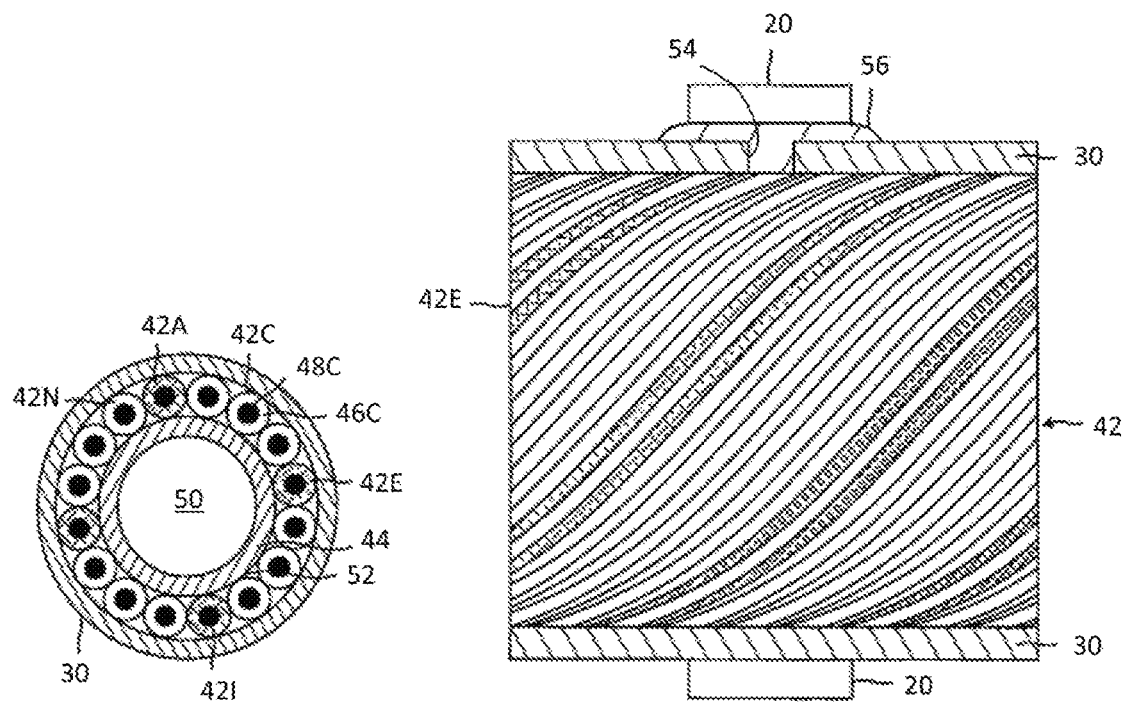
FIG. 6B
FIG. 6C

VARYING DIAMETER CATHETER DISTAL END DESIGN FOR DECREASED DISTAL HUB SIZE

FIELD OF THE PRESENT DISCLOSURE

This invention relates to electrophysiologic (EP) catheters, in particular, EP catheters for mapping and/or ablation in the heart.

BACKGROUND

Electrophysiology catheters are commonly-used for mapping electrical activity in the heart. Various electrode designs are known for different purposes. In particular, catheters having basket-shaped electrode arrays are known and described, for example, in U.S. Pat. Nos. 5,772,590, 6,748,255 and 6,973,340, the entire disclosures of each of which are incorporated herein by reference.

Basket catheters typically have an elongated catheter body and a basket-shaped electrode assembly mounted at the distal end of the catheter body. The basket assembly has proximal and distal ends and comprises a plurality of spines connected at their proximal and distal ends. Each spine comprises at least one electrode. The basket assembly has an expanded arrangement wherein the spines bow radially outwardly and a collapsed arrangement wherein the spines are arranged generally along the axis of the catheter body.

It is desirable that a basket assembly be capable of detecting in as few beats as possible, including a single beat, as much of the electrical function of the region in which the electrode assembly is deployed, such as the left or right atrium as possible. By implementing a greater number of electrodes in the electrode assembly, correspondingly greater and more complete coverage of the region may be obtained. Further, the increased number of electrodes may reduce or eliminate the need to reposition the electrode assembly to access all of the desired area in the region. Often, increasing the number of electrodes corresponds with an increase in the number of spines or other structures that support the electrodes. These spines are joined at a distal end by a central hub. As the device is deployed, a number of the distal electrodes may be put in a position that they are not in contact with the tissue. Additionally, the increase in the number of spines generally relates to an increase in the length and diameter of an elongated distal hub that is used to connect the spines. Devices that have a larger distal hub may be harder to deliver and deploy within a patient and may increase the risk of trauma to the tissue. As such, there is a need for a basket-shaped electrode assembly having an increased electrode density while maintaining a sufficiently minimized distal hub diameter and length that will improve the deployment and electrode contact within a chamber of a patient's heart. The techniques of this disclosure satisfy this and other needs as described in the following materials.

SUMMARY

The present disclosure is directed to a catheter including an elongated catheter body having proximal and distal ends and a basket-shaped electrode assembly at the distal end of the catheter body, the basket-shaped electrode assembly including a flexible wire assembly fashioned from a single piece of shape memory material. The flexible wire assembly includes a plurality of spines, each spine has a distal end and a proximal end and a distal hub, wherein the distal ends extend from the distal hub. The catheter further includes a plurality of electrodes and cabling attached to each spine; the plurality of electrodes and cabling having a corresponding plurality of wires coiled on a core and covered by a sheath such that each electrode is attached through the sheath to one of the plurality of wires and where the basket-shaped electrode assembly has an expanded arrangement where the spines bow radially outwardly and a collapsed arrangement where the spines are arranged generally along a longitudinal axis of the catheter body.

In one aspect, the distal hub further includes a stress-relieving edge, which may have a scalloped shape or a saw-tooth shape.

In one aspect, the single piece of shape memory material comprises a nitinol alloy tube or a sheet of nitinol alloy.

In one aspect, the distal hub has a height that is approximately equal to a thickness of the nitinol alloy tube or has a height that is approximately equal to two times the thickness of the nitinol alloy tube.

In one aspect, the basket-shaped electrode assembly comprises at least six, eight, ten or twelve spines, and each spine has at least ten electrodes or at least sixteen electrodes.

In one aspect, the basket-shaped electrode assembly has at least twelve spines, each spine comprises at least sixteen electrodes and the catheter body has a diameter less than approximately 10 french.

In one aspect, further includes a lumen configured to deliver irrigation fluid to the basket-shaped electrode assembly.

In one aspect, a catheter is made by the steps of forming an elongate catheter body; forming a flexible wire assembly by laser cutting a single piece of a shape memory material into a plurality of spines and a connecting distal hub; laser cutting a stress-relieving edge onto a distal end of the distal hub at a location opposite of the plurality of spines; heating the flexible wire assembly to heat set a basket-shaped arrangement; operably connecting a plurality of electrodes and cabling to each of the plurality of spines to form a basket-shaped electrode assembly; and operably connecting the basket shaped electrode assembly to a distal end of the elongate catheter body.

In one aspect, where the single piece of shape memory material comprises a nitinol alloy tube or a sheet of nitinol alloy and the distal hub has a height that is approximately equal to a thickness of the nitinol alloy tube.

In one aspect, the stress-relieving edge is a scalloped edge.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which:

FIG. 6A is a top view of a cabling of a spine of a basket-shaped electrode assembly with part(s) broken away, according to one embodiment.

FIG. 6B is an end cross-sectional view of the cabling of FIG. 6A.

FIG. 6C is a side view of the cabling of FIG. 6A, with part(s) broken away.

DETAILED DESCRIPTION

Figure 1:
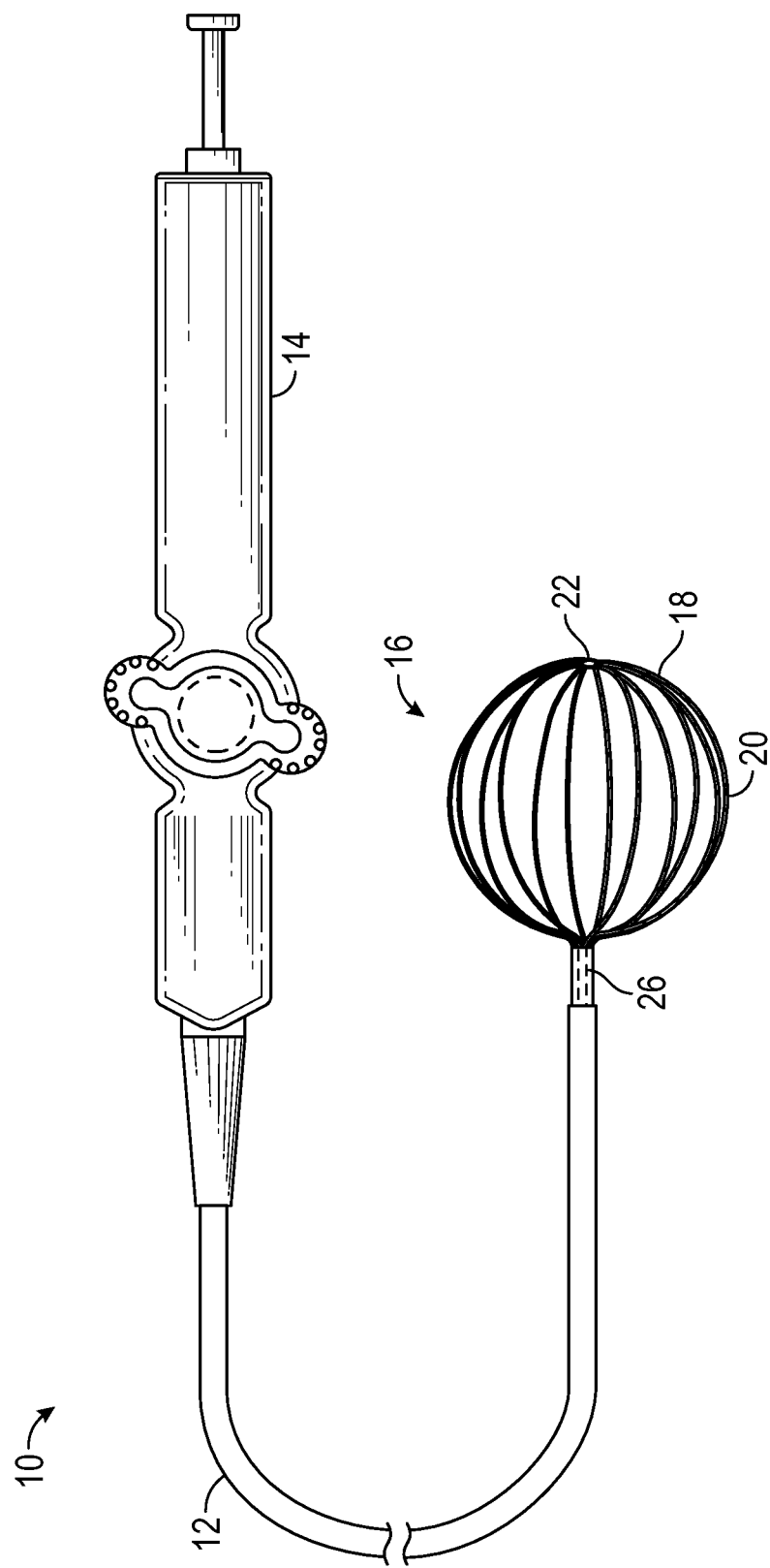
FIG. 1 is a top plan view of a catheter of the present invention, according to one embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a", "an" and "the" include plural referents unless the content clearly dictates otherwise.

Certain types of electrical activity within a heart chamber are not cyclical. Examples include arterial flutter or arterial fibrillation, and ventricular tachycardia originating in scars in the wall of the ventricle that have resulted from infarcts. Such electrical activity is random from beat to beat. To analyze or 'map' this type of electrical activity, it is desirable to obtain the 'picture' as quickly as possible, such as within one heartbeat. In other words, all the points of the map or picture may be obtained simultaneously within one-tenth of a second. According to the techniques of this disclosure, a basket-shaped electrode assembly having a high electrode density with improved electrode-to-tissue contact may be used to accurately map this electrical activity.

As shown in FIG. 1, the catheter 10 comprises an elongated catheter body 12 having proximal and distal ends and a control handle 14 at the proximal end of the catheter body, with a basket-shaped electrode assembly 16 having a plurality of spines 18, each carrying multiple electrodes 20, mounted at the distal end of the catheter body 12. The catheter body 12 comprises an elongated tubular construction having a single, axial or central lumen 26, but can optionally have multiple lumens if desired. To enable accurate mapping of electrical signals, for example to detect most or substantially all of the electrical function of the right or left atrium in as little as a single heartbeat, it may be desirable to provide an array of electrodes with a relatively high density. As such, the number of spines 18 employed may be six, eight, ten, twelve or any other suitable number. The distal ends of spines 18 are joined together at a distal hub 22. Distal hub 22 is a generally circular and flat structure to allow for more of the electrodes 20 to contact the tissue to be mapped. Spines 18 may be evenly or unevenly distributed radially about distal hub 22. Further, each spine 18 may include multiple electrodes 20, such as at least ten and up to approximately 16 electrodes per spine. Similarly, the electrodes may be evenly distributed along the spine or may be skewed proximally, centrally or distally to facilitate analysis of the measured electrical signals.

The catheter body 12 is flexible, i.e., bendable, but substantially non-compressible along its length. The catheter body 12 can be of any suitable construction and made of any suitable material. One construction comprises an outer wall made of polyurethane or PEBAX® (polyether block amide). The outer wall comprises an imbedded braided mesh of stainless steel or the like to increase torsional stiffness of the catheter body 12 so that, when the control handle 14 is rotated, the distal end of the catheter body will rotate in a corresponding manner. The outer diameter of the catheter body 12 is not critical, but generally should be as small as possible and may be no more than about 10 french depending on the desired application. In one aspect, the overall diameter of the catheter body 12 may relate to the number of electrodes 20 implemented by basket-shaped electrode assembly 16 in order to accommodate the associated electrical leads. For example, a twelve-spine design with each spine carrying sixteen electrodes for a total of 192 electrodes, a ten-spine design with each spine carrying sixteen electrodes for a total of 160 electrodes and an eight-spine design with each spine carrying sixteen electrodes for a total of 128 electrodes may utilize up to a 10.0 french catheter body. Likewise the thickness of the outer wall is not critical, but may be thin enough so that the central lumen can accommodate a puller wire, lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

Figure 2:
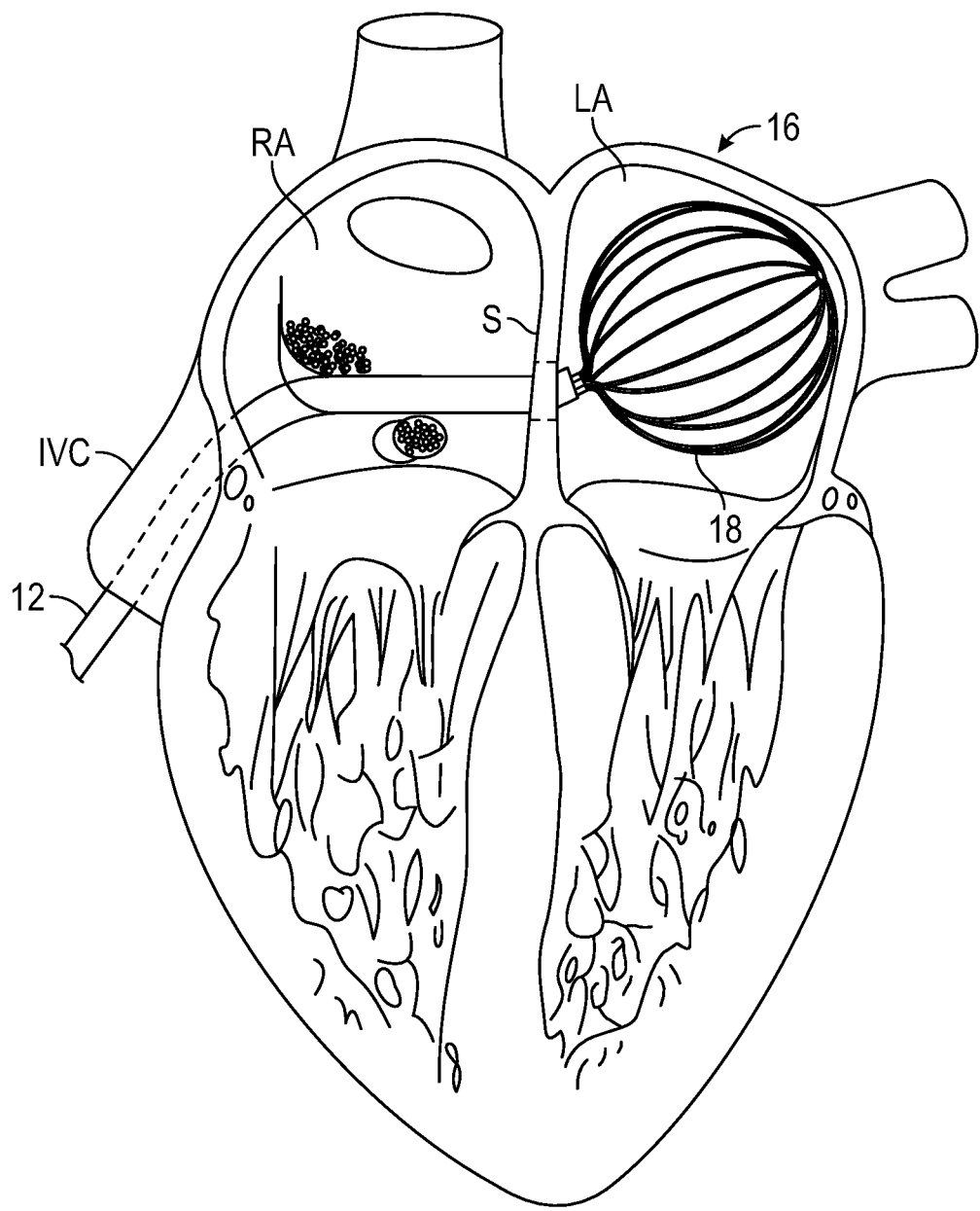
FIG. 2 is a schematic view of the basket-shaped electrode assembly of FIG. 1 deployed in the left atrium.

Spines 18 include a shape memory material, as described below, that facilitates assuming an expanded arrangement. As shown in FIG. 2, when the basket-shaped electrode assembly 16 assumes the expanded configuration, spines 18 bow outwards into contact or closer proximity with the walls of the chamber in which it has been deployed, such as the left atrium.

In one aspect, an electrophysiologist may introduce a guiding sheath, guidewire and dilator into the patient, as is generally known in the art. As an example, a suitable guiding sheath for use in connection with the inventive catheter is a 10 french DiRex™ Guiding Sheath (commercially available from BARD, Murray Hill, N.J.). The guidewire is inserted, the dilator is removed, and the catheter is introduced through the guiding sheath whereby the guidewire lumen 26 permits the catheter to pass over the guidewire. In one exemplary procedure as depicted in FIG. 2, the catheter is first introduced to the right atrium (RA) via the inferior vena cava (IVC), where it passes through the septum (S) in order to reach the left atrium (LA).

As will be appreciated, the guiding sheath covers the spines 18 of the basket-shaped electrode assembly 16 in a collapsed position so that the entire catheter can be passed through the patient's vasculature to the desired location. Once the distal end of the catheter reaches the desired location, e.g., the left atrium, the guiding sheath is withdrawn to expose the basket-shaped electrode assembly 16. Upon withdrawal of the guiding sheath, the shape memory material of the basket-shaped electrode assembly radially expands the device within the chamber. With the basket-shaped electrode assembly 16 radially expanded, the ring electrodes 20 contact atrial tissue. As recognized by one skilled in the art, the basket-shaped electrode assembly 16 may be fully or partially expanded, straight or deflected, in a variety of configurations depending on the configuration of the region of the heart being mapped.

When the basket-shaped electrode assembly 16 is expanded, the electrophysiologist may map local activation time and/or ablate using electrodes 20, which can guide the electrophysiologist in diagnosing and providing therapy to the patient. The catheter may include one or more reference ring electrodes mounted on the catheter body and/or one or more reference electrodes may be placed outside the body of the patient. By using the catheter with the multiple electrodes on the basket-shaped electrode assembly, the electrophysiologist can obtain a true anatomy of a cavernous region of the heart, including an atrium, allowing a more rapid mapping of the region.

As used herein, the term "basket-shaped" in describing the electrode assembly 16 is not limited to the depicted configuration, but can include other designs, such as spherical or egg-shaped designs, that include a plurality of expandable arms or spines connected, directly or indirectly, at their proximal and distal ends. In one aspect, different sized basket-shaped electrode assemblies may be employed depending on the patient's anatomy to provide a close fit to the area of the patient being investigated, such as the right or left atria.

Figure 3:
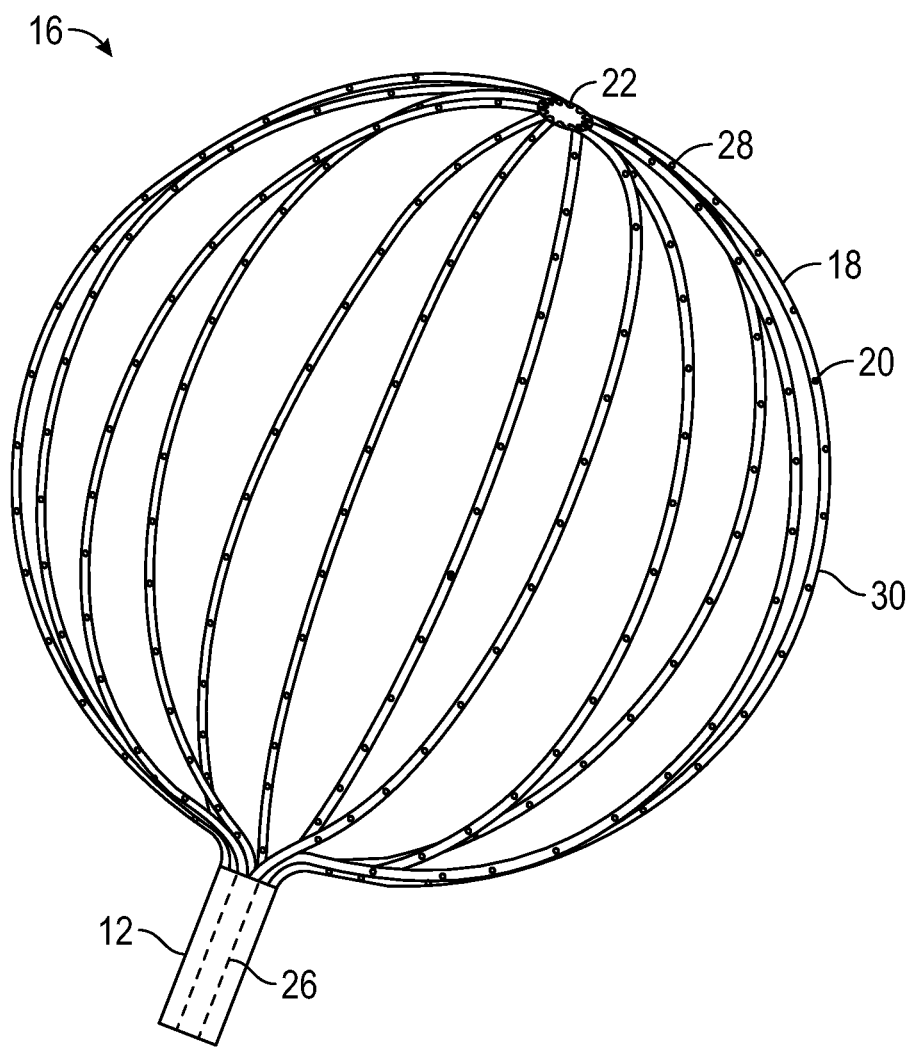
FIG. 3 is a schematic view of a basket-shaped electrode assembly, according to one embodiment.

A detailed view of one embodiment of the basket-shaped electrode assembly 16 is shown in FIG. 3, featuring a total of twelve spines 18, each carrying sixteen electrodes 20. As noted above, in other embodiments, different numbers of spines 18 and/or electrodes 20 may be employed, each of which may be evenly or unevenly distributed as desired. The distal ends of the spines 18 are joined at distal hub 22. Correspondingly, the proximal ends of the spines 18 may be secured to the distal end of the catheter body 12. Lumen 26 may be used as a guidewire lumen. In some embodiments, lumen 26 may also be used to supply a suitable irrigation fluid, such as heparinized saline, to the basket-shaped electrode assembly 16. A fitting (not shown) in the control handle 14 may be provided to conduct irrigation fluid from a suitable source or pump into the lumen 26.

Each spine 18 may comprise a flexible wire 28 with a non-conductive covering 30 on which one or more of the ring electrodes 20 are mounted. In an embodiment, the flexible wires 28 may be formed from a shape memory material to facilitate the transition between expanded and collapsed arrangements and the non-conductive coverings 30 may each comprise a biocompatible plastic tubing, such as polyurethane or polyimide tubing. A plurality of flexible wires 28 may be joined to form a flexible wire assembly 29.

Figure 4:
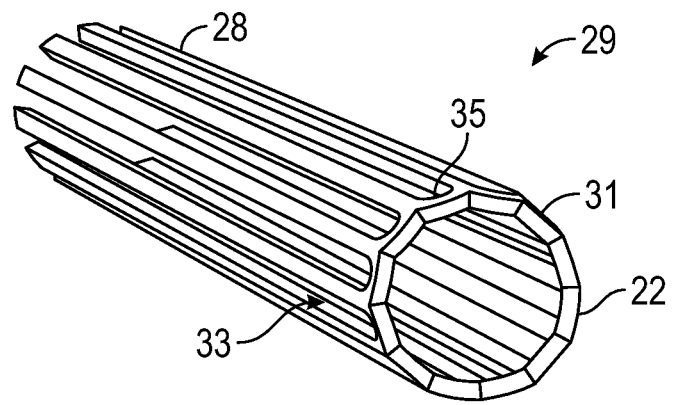
FIG. 4 is a schematic view of a flexible-wire component of the basket-shaped electrode assembly of FIG. 3.
Figure 5:
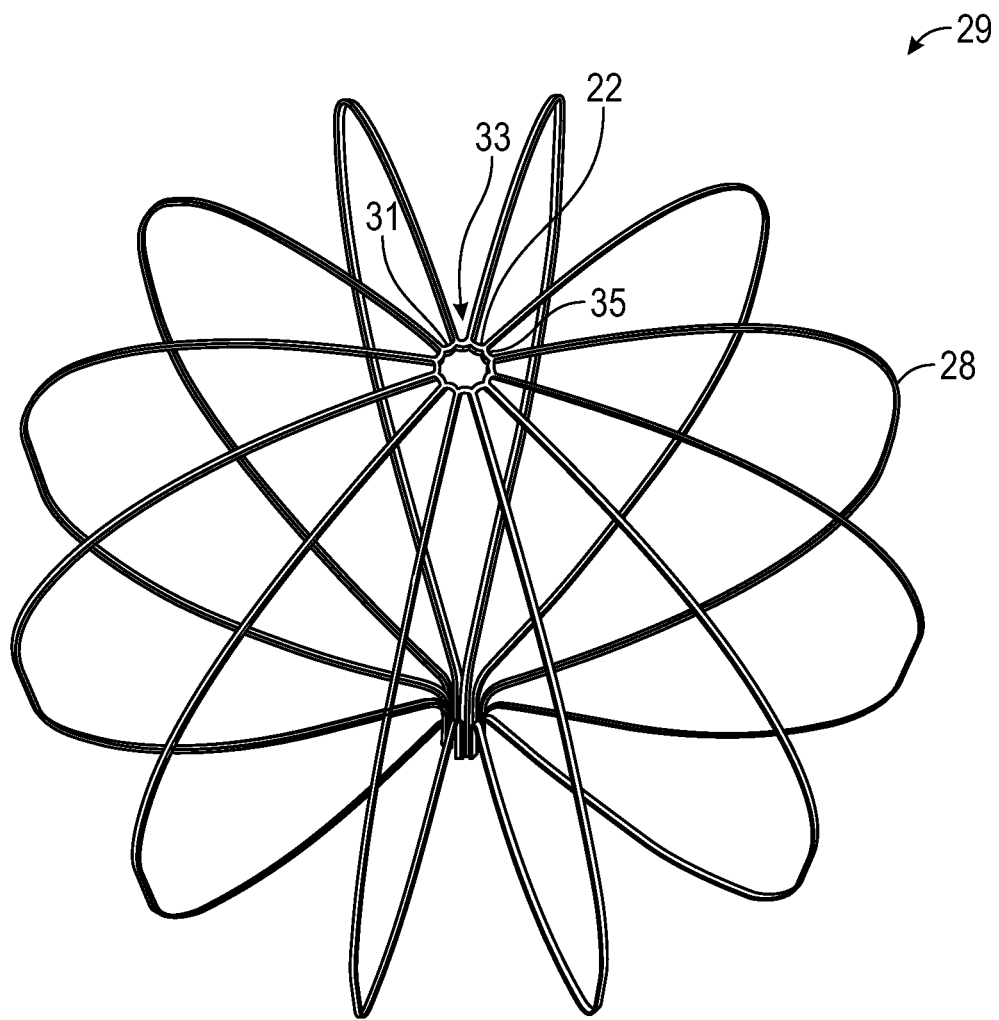
FIG. 5 is a schematic view of an expanded flexible-wire component of the basket-shaped electrode assembly, according to one embodiment.

FIGS. 4 and 5 illustrate one embodiment of a flexible wire assembly 29. Flexible wire assembly 29 comprises a plurality of flexible wires 28. The distal ends of each flexible wire 28 are joined at distal hub 22. In one embodiment, flexible wire assembly 29 is composed of Nitinol, a nickel-titanium alloy. As illustrated in FIG. 4, in one embodiment, flexible wire assembly 29 is formed from a single cylindrical tube of nitinol. In this embodiment, the nitinol tube has an outer diameter of 2.59 mm (0.102") and an inner diameter of 2.18 mm (0.086"). In one example, the outer diameter is no greater than 10 french. Additionally, the nitinol tube has a length between 1 mm (0.039 inch) and 20 mm (0.79 inch) that is sufficient to form the spines. One of ordinary skill in the art will appreciate that the length of the spines may vary and will correspond to the size of the chamber into which the device is deployed.

As mentioned above, the flexible wire assembly 29 is formed from a single tube. In one embodiment the nitinol tube is cut using standard cutting techniques such as laser cutting or etching. Other known methods of forming the nitinol tube into the flexible wire assembly 29 may be used. Using an appropriate laser, the spines 18 and distal hub 22 are cut from the tube as a single unit. The individual spines 18 are cut into the tube leaving material that will form the distal hub 22. In one embodiment, the height of the distal hub 22 is the same dimension as the thickness of the nitinol tube from which the assembly is cut. In this embodiment, the height of the distal hub 22 is reduced as compared to the prior art. During use, the dimension of the distal hub 22 allows more of the electrodes to come in contact with the chamber, making the mapping of the chamber faster and more accurate.

The process of forming the tube into the flexible wire assembly 29 also includes forming a stress-relieving edge 31 on hub 22. The stress-relieving edge 31 is a shaped edge to facilitate movement of the basket-shaped electrode assembly 16 from a delivery arrangement to a deployed arrangement. As illustrated in FIGS. 4 and 5, the stress relieving edge 31 comprises a scalloped shaped edge on the distal end of the flexible wire assembly 29. The formation of this edge reduces the amount of material on the distal hub. This reduction of material allows for the spines to expand into the basket-shape with a lesser amount of stress on the distal hub 22. It will be appreciated that as the spines 18 expand, the shaped edge 31 of the distal end of the distal hub moves inwardly so that the inner diameter of the distal hub 22 reduces in size. Thus, the removal of this material will reduce the stress and strain on the hub as it is moved from a delivery arrangement to a deployed arrangement. Further, any sharp edges on the scalloped edge are smoothed in order to prevent tissue damage during use. Other geometries for this stress-relieving edge include, for example, a saw-tooth edge and a truncated pyramid edge.

FIGS. 4 and 5 further illustrate that a proximal portion 33 of the distal hub 22 may include another stress relieving edge 35. In one embodiment, as electrode assembly 16 moves from a delivery configuration (FIG. 4) to a deployed configuration (FIG. 5) the proximal portion 33 of distal hub 22 becomes the outer diameter of the deployed distal hub. To further reduce the stress from the movement of the device during deployment, material from the proximal edge of the distal hub may be removed. As an example, the space between spines may have a semicircular or arch shape, as shown in FIG. 5. So, as the inner diameter of the distal hub decreases during expansion of the spines 18, the outer diameter of the proximal portion of the hub increases. Removal of the outer diameter material will further reduce the stress during this process.

The geometry of the flexible wire assembly 29 also reduces the stress caused by the manufacturing process. Heat treatment of the flexible wire assembly 29, once the device is formed into the basket-shape, creates a heat-treatment stress. This stress is reduced due to the geometry of the distal hub 22. At body temperature, nitinol wire is flexible and elastic and, like most metals, nitinol wires deform when subjected to minimal force and return to their shape in the absence of that force. Nitinol belongs to a class of materials called Shaped Memory Alloys (SMA) that have interesting mechanical properties beyond flexibility and elasticity, including shape memory and superelasticity which allow nitinol to have a "memorized shape", (e.g. the basket-shape), that is dependent on its temperature phases. The austenite phase is nitinol's stronger, higher-temperature phase, with a simple cubic crystalline structure. Superelastic behavior occurs in this phase (over a 50°–60° C. temperature spread). FIG. 5 illustrates the flexible wire assembly in the "memorized shape" or basket-shape. During manufacture, the nitinol tube (FIG. 4) is heated and formed into the basket-shape. This shape is then heat set, as is known in the art. Correspondingly, the martensite phase is a relatively weaker, lower-temperature phase with a twinned crystalline structure. When a nitinol material is in the martensite phase, it is relatively easily deformed and will remain deformed. However, when heated above its austenite transition temperature, the nitinol material will return to its pre-deformed shape, producing the "shape memory" effect. The temperature at which nitinol starts to transform to austenite upon heating is referred to as the "As" temperature. The temperature at which nitinol has finished transforming to austenite upon heating is referred to as the "Af" temperature. Accordingly, the basket-shaped electrode assembly 16 may have a three dimensional shape that can be easily collapsed to be fed into a guiding sheath and then readily returned to its expanded shape memory configuration upon delivery to the desired region of the patient upon removal of the guiding sheath.

FIGS. 4 and 5 illustrate a device cut from a single nitinol tube. In other embodiments, the flexible wire assembly is manufactured from a sheet of nitinol material, shaped and heat set into the desired "memorized" shape.

In a further aspect, each spine 18 may include cabling 40 with built-in or embedded lead wires 42 for the electrodes 20 carried by the spine as shown in FIGS. 6A-C. The cabling has a core 44, and a plurality of generally similar wires 42 each covered by an insulating layer 46 that enables each wire to be formed and to function as a conductor 48. The core 44 provides a lumen 50 in which can pass other components such as a support structure in the form of flexible wire 28 and/or additional lead wire(s), cables, tubing or other components.

In the following description, generally similar components associated with cabling 40 are referred to generically by their identifying component numeral, and are differentiated from each other, as necessary, by appending a letter A, B, . . . to the numeral. Thus, wire 42C is formed as conductor 48C covered by insulating layer 46C. While embodiments of the cabling may be implemented with substantially any plurality of wires 42 in the cabling, for clarity and simplicity in the following description cabling 40 is assumed to comprise N wires 42A, 42B, 42C, . . . 42N, where N equals at least the number of ring electrodes on each respective spine 18 of the basket-shaped electrode assembly 16. For purposes of illustration, insulating layers 46 of wires 42 have been drawn as having approximately the same dimensions as conductors 48. In practice, the insulating layer is typically approximately one-tenth the diameter of the wire.

The wires 42 are formed over an internal core 44, which is typically shaped as a cylindrical tube. The core material is typically selected to be a thermoplastic elastomer such as a polyether block amide or PEBAX®. Wires 42 are formed on an outer surface 52 of the core 44 by coiling the wires around the tube. In coiling wires 42 on the surface 52, the wires are arranged so that they contact each other in a "close-packed" configuration. Thus, in the case that core 44 is cylindrical, each wire 42 on the outer surface is in the form of a helical coil, configured in a multi-start thread configuration. For example, in the case of the N wires 42 assumed herein, wires 42 are arranged in an N-start thread configuration around core 44.

In contrast to a braid, all helical coils of wires 42 herein have the same handedness (direction of coiling). Moreover, wires in braids surrounding a cylinder are interleaved, so are not in the form of helices. Because of the non-helical nature of the wires in braids, even braid wires with the same handedness do not have a threaded form, let alone a multi-start thread configuration. Furthermore, because of the lack of interleaving in arrangements of wires in embodiments of the cabling, the overall diameter of the cabling produced is less than that of cabling using a braid, and the reduced diameter is particularly beneficial when the cabling is used for a catheter.

Once wires 42 have been formed in the multi-start thread configuration described above, the wires are covered with a protective sheath, such as in the form of the non-conductive covering 30 described above. The protective sheath material is typically selected to be a thermoplastic elastomer such as for example, 55D PEBAX without additives so that it is transparent. In that regard, the insulating layer 46 of at least one of wires 42 may be colored differently from the colors of the remaining wires as an aid in identifying and distinguishing the different wires.

The process of coiling wires 42 around the core 44, and then covering the wires by the non-conductive covering 30 essentially embeds the wires within a wall of cabling 40, the wall comprising the core and the sheath. Embedding the wires within a wall means that the wires are not subject to mechanical damage when the cabling is used to form a catheter. Mechanical damage is prevalent for small wires, such as 48 AWG wires, if the wires are left loose during assembly of a catheter.

In use as a catheter, an approximately cylindrical volume or lumen 50 enclosed by the core 44, that is afforded by embedding smaller wires (such as the 48 AWG wires) in the wall, allows at least a portion of the lumen 50 to be used for other components. It is understood that the plurality of wires 42 shown in the drawings is representative only and that a suitable cabling provides at least a plurality of wires equal to or greater than the plurality of ring electrodes mounted on each cabling or spine of the assembly. Cabling suitable for use with the present invention is described in U.S. application Ser. No. 13/860,921, filed Apr. 11, 2013, entitled HIGH DENSITY ELECTRODE STRUCTURE, and U.S. application Ser. No. 14/063,477, filed Oct. 25, 2013, entitled CONNECTION OF ELECTRODES TO WIRES COILED ON A CORE, the entire disclosures of which have been incorporated above. Each cabling 40 (with embedded lead wires 42) may extend to the control handle 14 for suitable electrical connection of wires 42, thereby allowing signals measured by electrodes 20 to be detected.

As noted, each spine 18 and cabling 40 pair carries a plurality of ring electrodes 20, which may be configured as monopolar or bipolar, as known in the art. Cabling 40 is schematically shown by a top view in FIG. 6A and by a side view in FIG. 6C, in which portions of non-conductive covering 30 have been cut away to expose wires 42 of the cabling 40, as well as to illustrate the attachment of a ring electrode 20 to the cabling 40. FIG. 6A illustrates cabling 40 prior to attachment of electrode 20, while FIG. 6C illustrates the cabling after the ring electrode has been attached. The ring electrodes 20 may have suitable dimensions to allow them to be slid over sheath 54.

The attachment point for each electrode 20 may be positioned over one or more of the wires 42, such as wire 42E in the illustrated example. A section of non-conductive covering 30 above the wire 42E and a corresponding section of insulating layer 46E are removed to provide a passage 54 to conductor 48E. In a disclosed embodiment, conductive cement 56 may be fed into the passage, ring electrode 20 may then be slid into contact with the cement, and finally the electrode may be crimped in place. Alternatively, the ring electrode 20 may be attached to a specific wire 42 by pulling the wire through non-conductive covering 30, and resistance welding or soldering the ring electrode to the wire.

In another embodiment, basket-shaped electrode assembly may include an expander. The expander (not shown) may comprise a wire or hypotube formed from a suitable shape memory material, such as a nickel titanium alloy. As will be appreciated, different relative amounts of movement of the expander 22 along the longitudinal axis may affect the degree of bowing, such as to enable the spines 18 to exert greater pressure on the atrial tissue for better contact between the tissue and the electrodes on the spines. Thus, a user can change the shape of the electrode assembly by adjusting the longitudinal extension or withdrawal of the expander.

Figure 7:
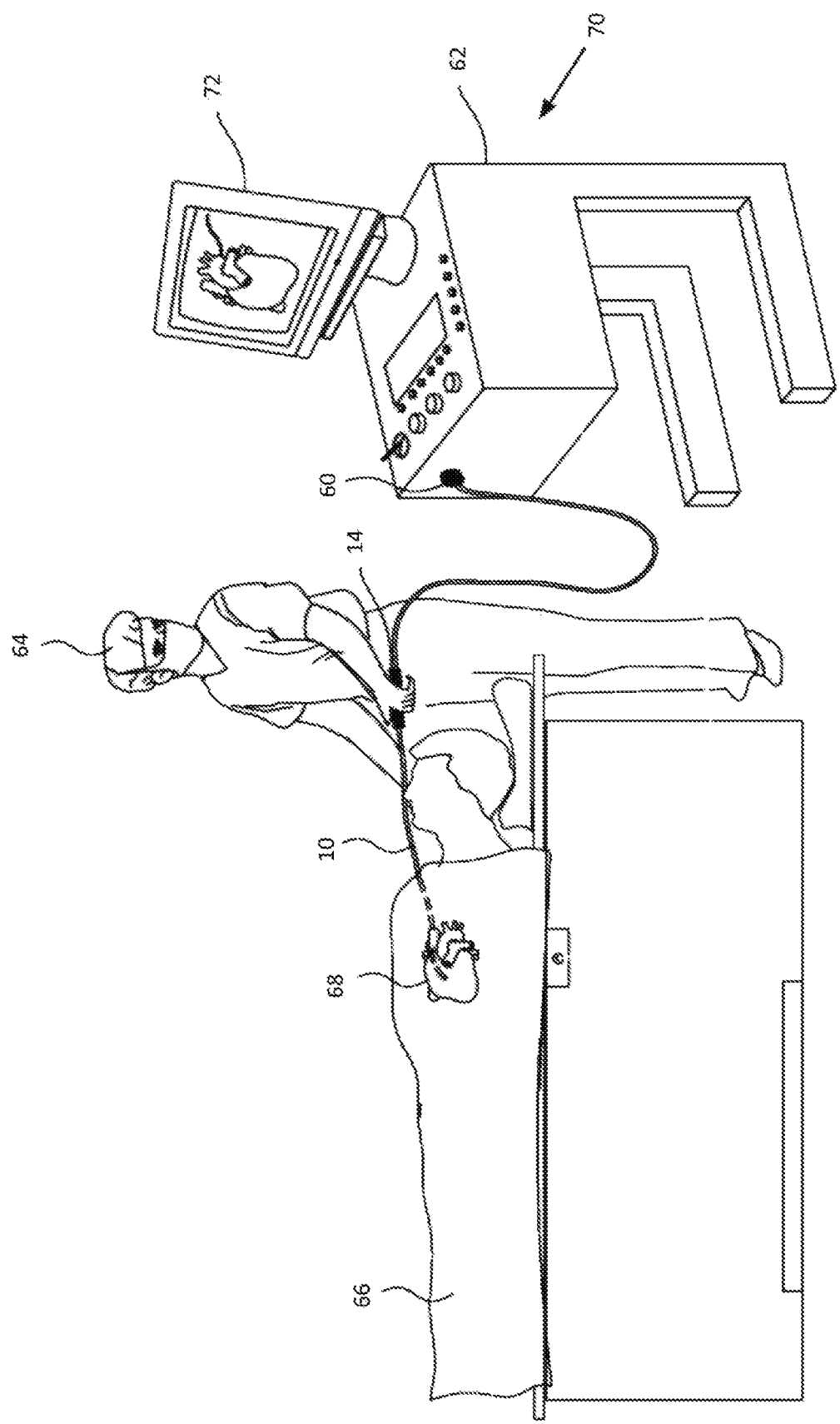
FIG. 7 is a schematic illustration of an invasive medical procedure using a basket-shaped electrode assembly, according to one embodiment.

To help illustrate use of the basket-shaped electrode assembly 16, FIG. 7 is a schematic depiction of an invasive medical procedure, according to an embodiment of the present invention. Catheter 10, with the basket-shaped electrode assembly 16 (not shown in this view) at the distal end may have a connector 60 at the proximal end for coupling the wires 42 from their respective electrodes 20 (neither shown in this view) to a console 62 for recording and analyzing the signals they detect. An electrophysiologist 64 may insert the catheter 10 into a patient 66 in order to acquire electropotential signals from the heart 68 of the patient. The professional uses the control handle 14 attached to the catheter in order to perform the insertion. Console 62 may include a processing unit 70 which analyzes the received signals, and which may present results of the analysis on a display 72 attached to the console. The results are typically in the form of a map, numerical displays, and/or graphs derived from the signals. With the inventive catheter, the map from the basket-shaped electrode assembly 16 is improved due to the reduction in the distal hub 22 dimensions, allowing more of the electrodes to contact the chamber.

In a further aspect, the processing unit 70 may also receive signals from one or more location sensors 74 provided near a distal end of the catheter 10 adjacent the basket-shaped electrode assembly 16 as schematically indicated in FIG. 1. The sensor(s) may each comprise a magnetic-field-responsive coil or a plurality of such coils. Using a plurality of coils enables six-dimensional position and orientation coordinates to be determined. The sensors may therefore generate electrical position signals in response to the magnetic fields from external coils, thereby enabling processor 70 to determine the position, (e.g., the location and orientation) of the distal end of catheter 10 within the heart cavity. The electrophysiologist may then view the position of the basket-shaped electrode assembly 16 on an image the patient's heart on the display 72. By way of example, this method of position sensing may be implemented using the CARTO™ system, produced by Biosense Webster Inc. (Diamond Bar, Calif.) and is described in detail in U.S. Pat. Nos. 5,391,199, 6,690,963, 6,484,118, 6,239, 724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference. As will be appreciated, other location sensing techniques may also be employed. If desired, at least two location sensors may be positioned proximally and distally of the basket-shaped electrode assembly 16. The coordinates of the distal sensor relative to the proximal sensor may be determined and, with other known information pertaining to the curvature of the spines 18 of the basket-shaped electrode assembly 16, used to find the positions of each of the electrodes 20.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
    an elongated catheter body extending along a longitudinal axis, the elongated catheter body having a proximal end and a distal end;
    a flexible wire assembly positioned at the distal end of the elongated catheter body formed from a single piece of shape memory material, the flexible wire assembly having a plurality of spines, each spine having a proximal end and a distal end, each distal end extending from a distal hub having a stress-relieving edge;
    a plurality of electrodes and cabling attached to each spine, the plurality of electrodes and cabling having a corresponding plurality of wires coiled on a core and covered by a sheath such that each electrode is attached through the sheath to one of the plurality of wires, such that the catheter has one operational state wherein the spines bow radially outwardly from the distal hub and another operational state wherein the spines are arranged generally along a longitudinal axis of the catheter body.

2. The catheter of claim 1, wherein the stress-relieving edge comprises a scalloped edge.

3. The catheter of claim 1, wherein the stress-relieving edge comprises a saw-toothed edge.

4. The catheter of claim 1, wherein the single piece of shape memory material comprises a nitinol alloy tube.

5. The catheter of claim 4, wherein the distal hub has a height that is approximately equal to a thickness of the nitinol alloy tube.

6. The catheter of claim 4, wherein the distal hub has a height that is approximately equal to two times the thickness of the nitinol alloy tube.

7. The catheter of claim 1, wherein the single piece of shape memory material comprises a sheet of nitinol alloy.

8. The catheter of claim 1, wherein the flexible wire assembly comprises at least six spines.

9. The catheter of claim 1, wherein the flexible wire assembly comprises at least ten spines.

10. The catheter of claim 1, wherein the flexible wire assembly comprises at least twelve spines.

11. The catheter of claim 1, wherein each spine comprises at least eight electrodes.

12. The catheter of claim 1, wherein each spine comprises at least sixteen electrodes.

13. The catheter of claim 1, wherein the catheter body has a diameter less than approximately 10 french and the flexible wire assembly comprises at least twelve spines, each spine having at least sixteen electrodes.

14. The catheter of claim 1, wherein the catheter body further comprises a lumen configured to deliver irrigation fluid to the flexible wire assembly.

15. A method for forming a catheter comprising:
forming an elongate catheter body;
forming a plurality of spines and a connecting distal hub from a single piece of shape memory material, each spine having a proximal end and a distal end, each distal end extending from the distal hub;
forming a stress-relieving edge onto a distal end of the distal hub at a location opposite of the plurality of spines;
heating the flexible wire assembly to heat set a basket-shaped arrangement;
connecting a plurality of electrodes and cabling to each of the plurality of spines to form a basket-shaped electrode assembly, the plurality of electrodes and cabling having a corresponding plurality of wires coiled on a core and covered by a sheath such that each electrode is attached through the sheath to one of the plurality of wires, such that the catheter has one operational state wherein the spines bow radially outwardly from the distal hub and another operational state wherein the spines are arranged generally along a longitudinal axis of the catheter body; and
connecting the basket shaped electrode assembly to a distal end of the elongate catheter body.

16. The catheter of claim 15, wherein the single piece of shape memory material comprises a nitinol alloy tube.

17. The catheter of claim 16, wherein the distal hub has a height that is approximately equal to a thickness of the nitinol alloy tube.

18. The catheter of claim 15, wherein the single piece of shape memory material comprises a sheet of nitinol alloy.

19. The catheter of claim 15, wherein the stress-relieving edge is a scalloped edge.

* * * * *